US012343227B2

(12) United States Patent
Hillman

(10) Patent No.: US 12,343,227 B2
(45) Date of Patent: *Jul. 1, 2025

(54) DENTAL DEVICE FOR TOOTH WHITENING

(71) Applicant: ProBiora Health, LLC, Dallas, TX (US)

(72) Inventor: Jeffrey Daniel Hillman, Gainsville, FL (US)

(73) Assignee: ProBiora Health, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/097,414

(22) Filed: Jan. 16, 2023

(65) Prior Publication Data

US 2023/0225844 A1 Jul. 20, 2023

Related U.S. Application Data

(63) Continuation of application No. 15/662,232, filed on Jul. 27, 2017, now Pat. No. 11,564,785, which is a continuation of application No. 15/582,429, filed on Apr. 28, 2017, now Pat. No. 11,096,770, which is a continuation of application No. 12/482,881, filed on Jun. 11, 2009, now Pat. No. 9,636,196.

(60) Provisional application No. 61/061,264, filed on Jun. 13, 2008.

(51) Int. Cl.
| | |
|---|---|
| *A61C 19/06* | (2006.01) |
| *A61K 8/99* | (2017.01) |
| *A61K 35/744* | (2015.01) |
| *A61K 35/745* | (2015.01) |
| *A61K 35/747* | (2015.01) |
| *A61Q 11/00* | (2006.01) |

(52) U.S. Cl.
CPC .......... *A61C 19/063* (2013.01); *A61C 19/066* (2013.01); *A61K 8/99* (2013.01); *A61K 35/744* (2013.01); *A61K 35/745* (2013.01); *A61K 35/747* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,955,281 A * | 5/1976 | Weitzman | A61C 19/063 433/80 |
| 4,133,875 A | 1/1979 | Hillman | |
| 4,454,109 A | 6/1984 | Hillman | |
| 5,496,726 A | 3/1996 | Park et al. | |
| 5,607,672 A | 3/1997 | Hillman | |
| 5,894,017 A | 4/1999 | Sagel et al. | |
| 5,932,469 A | 8/1999 | Hillman | |
| 6,379,653 B1 | 4/2002 | Aaslyng | |
| 6,776,979 B2 | 8/2004 | Frager et al. | |
| 7,128,899 B2 | 10/2006 | Chen | |
| 7,931,892 B2 | 4/2011 | Hillman | |
| 8,865,156 B2 | 10/2014 | Hillman | |
| 2004/0101496 A1 | 5/2004 | Chen | |
| 2004/0136924 A1 | 7/2004 | Boyd et al. | |
| 2004/0166094 A1 | 8/2004 | Darouiche | |
| 2006/0045870 A1 | 3/2006 | Oh | |
| 2006/0246015 A1 | 11/2006 | Hillman | |
| 2009/0208543 A1 | 8/2009 | Nathoo | |
| 2011/0123461 A1 | 5/2011 | Hillman | |

FOREIGN PATENT DOCUMENTS

| | | | |
|---|---|---|---|
| CN | 1863464 | 11/2006 | |
| EP | 0058575 | 8/1982 | |
| EP | 0453097 | 3/1991 | |
| EP | 1585857 | 4/2005 | |
| WO | 95/31556 | 11/1995 | |
| WO | 96/40865 | 12/1996 | |
| WO | 96/040865 | 12/2000 | |
| WO | 0078322 | 12/2000 | |
| WO | 02/045727 | 6/2002 | |
| WO | WO-2007025244 A2 * | 3/2007 | ......... A61C 17/0205 |
| WO | 2008039531 A1 | 4/2008 | |

OTHER PUBLICATIONS

Byers, HL; et al; "Isolation and characterisation of sialidase from a strain of *Streptococcus oralis*" Journal of Medical Microbiology, 49, 235-244, 2000 (Year: 2000).*
Kraus, FW; et al; "Peroxide and peroxidogenic bacteria in human saliva" Journal of Bacteriology, 73, 727-735, 1957 (Year: 1957).*
Tielou et al., "The effect and research development of hydrogen peroxide in tooth bleaching", Foreign Medicine, Stomatology, 24(3):156-158 (1997).
Tielou et al., "The effect and research development of hydrogen peroxide in tooth bleaching", Foreign Medicine, Stomatology, 24(3):156-158 (1997), translation of first paragraph only.
Attin, et al., "Review of the current status of tooth whitening with the walking bleach technique", International Endodontic Journal, 36:313-329 (2003).
Fuerst et al., "Inactivation of Bacteria by Decay of Incorporated Radioactive Phosphorus", J. Gen. Physiol., vol. 40, No. 1, 73-90(1956).
Park et al., "Infection control by Antibody Disruption of Bacterial Quorum Sensing Signaling", Chemistry & Biology, vol. 14, 1119-1127 (2007).
Rubin, "Growth and mutation of bacteria during continuous irradiation", J. Bacteriol., vol. 67, No. 3, 361-368 (1954).
Boles, et al., "agr-Mediated Dispersal of *Staphylococcus aureus* Biofilms", Plos Pathogens, vol. 4, No. 4, 1-13 (2008).
International Search Report for PCT application No. PCT/US11/20826 dated Jun. 29, 2011.
U.S. Appl. No. 60/494,169, filed Aug. 11, 2003.
Loe, et al., "Early Onset of Periodontitis in the United States of America", Journal of Periodontology, 63:608-616 (1991).

(Continued)

*Primary Examiner* — David W Berke-Schlessel
(74) *Attorney, Agent, or Firm* — Fish IP Law, LLP

(57) ABSTRACT

Dental devices are described that include isolated, non-pathogenic, hydrogen peroxide-producing bacterial strains and genetically engineered LDH-deficient bacterial strains, which can be used to whiten teeth and treat periodontal disease.

11 Claims, 2 Drawing Sheets

(56) References Cited

OTHER PUBLICATIONS

Socransky, et al., "Associations between microbial species in subgingival plaque samples", Oral Microbiol. Immunol. 3:1-7 (1998).

Hillman, et al., "Interaction between wild-type, mutant and revertant forms of the bacterium Streptococcus sanguis and 4 the bacterium Actinobacillus Actinomycetemcomitans in vitro and the gnotobiotic rat", Archs. Oral Biol., vol. 33, No. 6, pp. 395-401 (1988).

Stashenko, et al., "Microftora of Plaque in Rats following infection with an LOH-Deficient mutant of Streptococcus rattus", Caries Res. 23:375-377 (1989).

Hillman, "Lactate Dehydrogenase mutants of Streptococcus mutans: Isolation and preliminary characterization", Infection and Immunity, vol. 21, Vo. 1, p. 206-212 (1978).

Abhyankar, et al., "Serotype c Streptococcus mutans mutatable to lactate dehydrogenase deficiency", J. Dent. Res., vol. 64, No. 11, pp. 1267-1271 (1985).

Johnson, et al., "Cariogenic potential in vitro in man and in vivo in the rate of lactate dehydrogenase mutants of Streptococcus mutans", Archs. Oral Biol., vol. 25, pp. 707-713 (1980).

Hillman, et al., "Acetoin Production by Wild-Type Strains and a Lactate Dehydrogenase—Deficient Mutant of Streptococcus mutans", Infection and Immunity, vol. 55, No. 6, p. 1399-1402 (1987).

Hillman, et al., "Cloning and Expression of the Gene Encoding the Fructose-1, 6-Diphosphate-Dependant L-(+)—Lactate Dehydrogenase of Streptococcus mutans", Infect. Immun., 58:1290-1295 (1990).

Hillman, et al., "The Relationships Between Streptococcal Species and Periodontopathic Bacteria in Human Dental Plaque", Archs. Oral Biol., 30:791-795 (1985).

Tagg, et al., "Bacterial replacement therapy: adapting 'germ warfare' to infection prevention", Trends in Biotechnology, vol. 21, No. 5, pp. 217-223 (2003).

Kreth, et al., Streptococcal Antagonism in Oral Biofilms: Streptococcu sanguinis and Streptococcus gordonii Interference with Streptococcus mutans, Journal of Bacteriology, Jul. 2008, p. 4632-4640. Vol. 190, No. 13, 9 pages.

Feuerstein, Osnat, et al. "Synergic antibacterial effect between visible light and hydrogen peroxide on Streptococcus mutans," Journal of Antimicrobial Chemotherapy (2006) 57, 872-876. 5 pages.

Chinese Office Action dated Dec. 5, 2017 for CN201610065409; 8 pages.

American Dental Association, "Tooth Whitening/Bleaching: Treatment Considerations for Dentists and Their Patients" dated Sep. 2009, 13 pages.

Gerlach et al., "A randomized clinical trial comparing a novel 5.3% hydrogen peroxide whitening strip to 10%, 15%, and 20% carbamide peroxide tray-based bleaching systems.", PubMed Compend Contin Educ Dent Suppl. 2000:(29):S22-8; quiz S42-3, 1 page.

Tong et al., "Streptococcus oligofermentans inhibits Streptococcus mutans through conversion of lactic acid into Inhibitory H2O2: a possible couteroffensive strategy for interspecies competitions", Molecular Microbiology (2007) 63 (3), 872-880.

Yalcin et al., "Bleaching-induced Colour Change in Plastic Filling Materials", Journal of Biomaterials Applications vol. 19—Jan. 2005, 9 pages.

ADA Council on Scientific Affairs, "Tooth Whitening/Bleaching: Treatment Considerations for Dentist and Their Patients", American Dental Association, dated Sep. 2009, 13 pages.

Hardy Diagnostics, "Instructions for Use Citerion Dextrose (Glucose)", dated 2020, 3 pages.

Mike Thimpson, "Glucose", Winchester College UK, 5 pages.

\* cited by examiner

DENTAL DEVICE FOR TOOTH WHITENING

This application is a continuation of U.S. patent application Ser. No. 15/662,232, filed Jul. 27, 2017, which is a continuation of U.S. Pat. No. 11,096,770, filed Apr. 28, 2017, which is a continuation of U.S. Pat. No. 9,636,196, issued May 2, 2017, which claims priority to U.S. Provisional Patent Application No. 61/061,264, filed Jun. 13, 2008, each of which is incorporated by reference herein in its entirety.

FIELD OF THE INVENTION

The field of the invention is devices and methods for whitening teeth.

BACKGROUND

Tooth surfaces are absorbent and can become stained or discolored by the use of tobacco products, eating or drinking certain foods and beverages (e.g., coffee, tea and red wine), the buildup of dental plaque, the process of aging, diseases, trauma, medications, congenital conditions, and other environmental effects. Teeth are comprised of an inner dentin layer, an outer enamel layer and an acquired pellicle. The acquired pellicle is a proteinaceous layer derived from saliva that forms on the surface of tooth enamel.

Extrinsic and intrinsic staining of the teeth can occur. Extrinsic staining is staining of the acquired pellicle that can occur when compounds such as tannins and polyphenolic compounds come in contact with teeth during eating, drinking or smoking. These compounds then become trapped in and tightly bound to the proteinaceous layer on the surface of the teeth. Extrinsic staining can be removed by mechanical methods of tooth cleaning, such as brushing or flossing and by chemical cleaning methods. Even with regular brushing and flossing, rapid or slow accumulation can develop into noticeable intrinsic tooth discoloration. Intrinsic staining can be caused by staining compounds that penetrate the enamel layer and the dentin layer or can arise from sources within the tooth. Intrinsic staining is difficult to remove and cannot typically be removed by mechanical methods of tooth cleaning, but high chemical concentrations and/or prolonged chemical cleaning methods can be used to remove some or all of this type of staining.

White, unstained teeth are considered cosmetically desirable. Teeth can be whitened by, for example, mechanical cleaning methods, veneers that are placed over the teeth, and chemical bleaching.

While tooth whitening products are known in the art, these products are traditionally used by those seeking the cosmetic benefit of whiter teeth. However, there is a different population of consumers who desire whiter teeth and/or more oral benefits including cleaner teeth, healthier gums, and decreased oral malodor. Therefore, there is a desire to provide oral hygiene products that can deliver oral care benefits in addition to tooth whitening. Furthermore, oral hygiene time is typically limited and so there is a desire to deliver these oral care benefits quickly and conveniently as part of a daily oral hygiene regimen.

BRIEF SUMMARY OF THE INVENTION

Compositions are provided that include hydrogen-peroxide producing bacterial species or strains and genetically modified LDH-deficient bacterial strains in formulation suitable for application to the oral cavity. Such compositions are useful in whitening teeth and in the treatment of periodontal disease.

Embodiments of the inventive concept include one or more isolated, non-pathogenic, hydrogen peroxide producing bacterial species or strains, and one or more genetically modified LDH-deficient bacterial strain(s). The isolated, non-pathogenic, hydrogen peroxide-producing bacterial species or strain can be *Lactobacillus*, Bifidobacteria, *viridans Streptococcus, Leuconostoc, Pediococcus*, and/or *Lactococcus*. Examples of suitable isolated, non-pathogenic, hydrogen peroxide-producing bacteria include isolated *Streptococcus oralis* strain and isolated *Streptococcus uberis*. The genetically modified LDH-deficient bacterial strain can be a genetically modified strain of *Streptococcus mutans*.

In some embodiments the composition can include a carrier. Such a carrier can be a solid-based, dry material. Examples such solid-based carriers include a solid food, a packaged food, a wafer, a tablet, a capsule, a lozenge, a powder, and/or a powdered food supplement. Alternatively, in other embodiments carrier is a liquid or a gel. In such embodiments the bacterial composition can be in the form of an aqueous solution, a physiological saline solution, a urea suspension or solution, an alcohol suspension or solution, a glycol suspension or solution, a viscous liquid, a paste, a gel, a solution, a dentifrice, a mouthwash, an oral rinse, a liquid suspension, and/or a chewing gum. In still other embodiments the carrier can be a dental device, such as a dental tray or a flexible strip.

In some embodiments the bacterial composition can include additional components. One suitable additional component is a metabolizable carbon source. Another suitable additional component is a nutritional supplement, such as a vitamin, a mineral, an amino acid, a carbohydrate, and/or a lipid. Another suitable additional component is a flavoring. Another suitable additional component is a gelling agent, such as a silicone, a polyethylene oxide, a polyvinyl alcohol, a poly alkyl vinyl ether-maleic acid copolymer (PVM/MA copolymer), a polyvinyl alcohol, a polyacrylic acid, a polyvinyl pyrrolidone-vinyl acetate copolymer, polyvinyl pyrrolidone, a carbomer or carboxypolymethylene, hydroxy propyl methyl cellulose, hydroxy ethyl cellulose, hydroxy propyl cellulose, corn starch, carboxymethyl cellulose, a gelatin, an alginate salt, and/or a natural gum. Still another suitable additional component is a humectant, such as glycerin, glycerol, sorbitol, polyethylene glycol, propylene glycol, and an edible polyhydric alcohol.

In some embodiments the bacterial composition can include dried bacteria, which can be produced by dehydration, spray drying, and/or freeze-drying. In other embodiments the bacterial composition can include microencapsulated bacteria. Such microencapsulated bacterial compositions can include a lipid material, such as a triacylglycerol, a wax, an organic ester, soybean oil, cottonseed oil, palm kernel oil, and/or an ester of a long-chain fatty acid.

DETAILED DESCRIPTION

Figure 1:
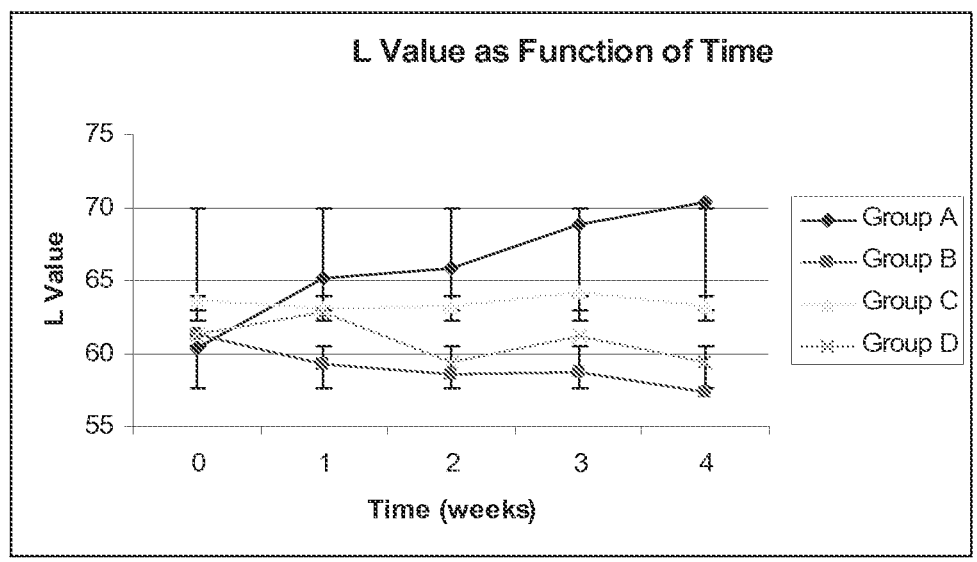
FIG. 1 shows the lightness values of stained dental ceramic discs over time. Group A (Experimental), Group B (plus catalase), Group C (minus dextrose), D (minus KJ3sm).

As used herein, the singular forms "a," "an", and "the" include plural referents unless the context clearly dictates otherwise.

The instant invention provides methods and compositions for the maintenance of oral health, including, for example, tooth whitening. A composition of the invention comprises one or more isolated, non-pathogenic, hydrogen peroxide-producing species or strains of bacteria, and optionally, LDH-deficient mutans Streptococcus. Certain bacteria can produce hydrogen peroxide at a level that can whiten teeth as demonstrated herein for the first time. A composition of the invention can influence or effect a desired change in appearance and/or structure of a tooth surface. Examples of appearance and structural changes include, but are not necessarily limited to, whitening, stain bleaching, stain removal, plaque removal, and tartar removal. Furthermore, a composition of the invention can provide additional oral care benefits such as treatment and/or prevention of dental caries, periodontitis, oral bacterial infections and diseases, oral wounds, Candida or fungal overgrowth, halitosis, or xerostomia-induced dental caries and associated periodontal diseases, the promotion of wound healing, or a combination thereof to a subject.

Compositions of the Invention The invention provides methods for whitening tooth surfaces using a composition comprising one or more non-pathogenic, hydrogen peroxide-producing viridans Streptococci species or strains, and/or one or more non-pathogenic, hydrogen peroxide-producing Lactobacillus species or strains and/or one or more non-pathogenic, hydrogen peroxide-producing Bifidobacteria species or strains and/or one or more non-pathogenic, hydrogen peroxide producing Lactococcus species or strains and/or one or more non-pathogenic, hydrogen peroxide producing Pediococcus species or strains and/or one or more non-pathogenic, hydrogen peroxide producing Leuconostoc species or strains. In one embodiment of the invention the bacterial strains can be generally recognized as safe (GRAS), and can transiently attach or adhere to a tooth surface by virtue of electrostatic interactions, van der Waals interactions, or protein or polysaccharide adhesins on the bacterial surface that recognize and interact with molecules present on the tooth surface. Examples of viridans Streptococci species include, but are not limited to S. sanguis, S. parasanguis, S. gordonii, S. oralis, S. uberis, S. mitis, S. rattus, S. salivariaus, S. vestibularis, S. angionosus, S. constellatus, S. intermedius, S. mutans, S. sobrinus, S. milleri, S. cricetus, and S. minor. Examples of Lactobacillus species include, but are not limited to, L. acidophilus, L. jensenii, L. catenaforme, L. leichrnanni, L. plantarum, L. johnsonii, L. gasseri, L. delbrueckii, L. casei, L. brevis, L. salivarius, L. gasseri, L. sobrius, L. rhamnosus, L. reuteri, L. fermenturn, L. paracasei, L. dextranicurn, and L. helveticus. Examples of Bifidobacteria species include, but are not limited to B. angulaturn, B. anirnalis, B. asteroides, B. bifidum, B. bourn, B. breve, B. catenulaturn, B. choerinurn, B. coryneforrne, B. cuniculi, B. dentiurn, B. gallicurn, B. gallinarurn, B indicurn, B. longum, B. magnum, B. meryci-cum, B. minimum, B. pseudocatenulaturn, B. pseudolon-gurn, B. psychraerophilurn, B. pullorurn, B. ruminantium, B. saeculare, B. scardovii, B. sirniae, B. subtile, B. ther-macidophilum, B. therrnophilum, and B. urinali. Examples of other non-pathogenic bacteria that can produce hydrogen peroxide include, without limitation, Pediococcus species, such as P. acidilactici, Leuconostoc species, such as L. mesenteroides, Lactococcus species such as L. iactis.

The quantity of hydrogen peroxide produced by bacteria can be experimentally determined. See e.g., Hillman and Shivers, Arch. Oral. Biol., 33:395-401 (1988). The culture liquor of cells grown in the presence of oxygen is incubated with 40 μg/ml horseradish peroxidase and 0.4 μmol/ml o-dianisidine. After 2 minutes, the reaction is stopped by the addition of 0.02 ml of 5N HCl. The optical density of the sample is measured at 410 nm and the hydrogen peroxide concentration of the sample is calculated from a standard curve prepared using authentic hydrogen peroxide and an extinction coefficient at 230 nm of $81M^{-1}$ $cm^{-1}$. In one embodiment of the invention the bacteria can produce at least about 0.5, 1, 2, 5 mM or more of $H_2O_2$ or any range or value between about 0.1 and about 5 mM.

In one embodiment of the invention a composition of the invention comprises one or more isolated Streptococcus oralis strains and/or one or more S. uberis strains. Compositions of the invention can optionally comprise one or more isolated strains or species of mutans Streptococcus that are LDH-deficient. The combination of non-pathogenic, hydrogen peroxide-producing bacteria and/or mutans Streptococcus provides a significant practical advantage in that the combination can used to prevent and treat, for example, dental caries, periodontitis, oral bacterial infections and diseases, oral wounds, Candida or fungal overgrowth, halitosis, or xerostomia-induced dental caries or periodontal disease, while also whitening the teeth.

Streptococcus oralis (previously known as S. sanguis Type II) and S. uberis are important components in maintaining the normal, healthy balance of microorganisms that comprise the periodontal flora. See Socransky et al., Oral Microbiol. Immunol. 3:1-7 (1988); Hillman and Shivers, Arch. Oral. Biol., 33:395-401 (1988); Hillman et al., Arch. Oral. Biol., 30:791-795 (1985). S. oralis can also be found in dental plaque and has been demonstrated to correlate with periodontal health, in particular by interfering with the colonization by periodontal pathogens such as Aggregetobacter actinomycetemcomitans, Porphyromonas gingivalis, Peptostreptococcus micros, and Campylobacter rectus. Compositions of the invention can comprise one or more isolated strains of S. oralis, for example, ATCC 35037, ATCC 55229, ATCC 700233, ATCC 700234 and ATCC 9811. Other strains of S. oralis include KJ3 and KJ3sm. KJ3sm is a naturally occurring genetic variant of KJ3 that is resistant to 1 mg/ml streptomycin. The streptomycin resistance is advantageous because it provides a marker for easy isolation of the bacteria. Additionally, streptomycin resistant strains are slightly attenuated and do not survive as long in an oral cavity as wild-type strains. This property is useful where the goal is to non-persistently colonize the oral cavity of an animal with the bacteria.

S. uberis can also be found in dental plaque and has been demonstrated to correlate with periodontal health, in particular by interfering with the colonization by periodontal pathogens such as Tannerella forsythensis, P. micros, C. rectus, and Prevotella melaninogenica. Compositions of the invention can comprise one or more isolated strains of S. uberis, for example, ATCC 13386, ATCC 13387, ATCC 19435, ATCC 27958, ATCC 35648, ATCC 700407, ATCC 9927, strain KJ2 or strain KJ2sm. KJ2sm is a naturally occurring genetic variant of KJ2 that is resistant to 1 mg/ml streptomycin and provides the same advantages as for streptomycin-resistant strains of S. oralis. One or more isolated strains of S. oralis or one or more isolated strains of S. uberis, or both, can be used in compositions and methods of the invention.

Compositions of the invention can comprise one or more isolated *mutans Streptococcus* bacteria species deficient in the production of lactic acid. These species include, for example, *S. rattus, S. cricetus, S. mutans, S. sobrinus, S. downeii, S. macacae,* and *S. ferus*. A *mutans Streptococcus* of the invention does not substantially produce L(+) lactate dehydrogenase (LDH). Such a strain is termed an LDH-deficient strain. An LDH-deficient strain of *mutans Streptococcus* produces 75%, 80%, 90%, 95%, 98%, 99%, or 100% less lactic acid than wild-type strains of *mutans Streptococcus*. An LDH-deficient *mutans Streptococcus* strain can be a naturally occurring strain of *mutans Streptococcus* or a genetically modified strain of *mutans Streptococcus*. LDH-deficient *mutans Streptococcus* can compete with and/or displace pathogenic bacteria such as *S. mutans*, a principal etiological agent of dental caries, in the oral cavity. LDH-deficient *mutans Streptococcus* stains will compete with *S. mutans* for the same nutrients, colonization sites, etc. Therefore, LDH-deficient *mutans Streptococcus* strains can be used to, for example, prevent and/or treat dental caries. LDH-deficient strains of *mutans Streptococcus* are non-pathogenic, alter the microenvironment of the oral cavity to prevent colonization or outgrowth of pathogenic organisms, and/or displace pathogenic organisms from the oral cavity where the pathogen is part of the host's indigenous flora.

Examples of LDH-deficient *mutans Streptococcus* strains include, for example, *S. rattus* JH145 (ATCC 31377) (a spontaneous, naturally-occurring LDH-deficient mutant) and JH140 (ATCC 31341) (a chemically-modified LDH-deficient mutant). See e.g., Stanshenko & Hillman, Microflora of plaque in rats following infection with an LDH-deficient mutant of *Streptococcus rattus*, Caries Res. 23:375-377 (1989); Hillman, Lactate dehydrogenase mutants of *Streptococcus mutans*: Isolation and preliminary characterization. Infect. Immun. 21:206-212 (1978); see also Abhyankar et al., Serotype c *Streptococcus mutans* mutatable to lactate dehydrogenase deficiency. J. Dent. Res. 64:1267-71 (1985).

An LDH-deficient strain of *mutans Streptococcus* can be derived from a *mutans Streptococcus* strain using, for example, chemical or physical mutagenesis techniques. Strains that are mutagenized using these techniques are considered genetically modified strains. For example, a *mutans Streptococcus* strain can be subjected to mutagens such as nitrous acid, formic acid, sodium bisulphate, UV light, base analog mutagens, including for example, 5-bromo-deoxyuridine (5BU), alkylators such as ethyl methane sulfonate (EMS), methyl methane sulfonate (MMS), diethylsulfate (DES), and nitrosoguanidine (NTG, NG, MNNG). See e.g., In Vitro Mutagenesis Protocols, Braman, Ed., Humana Press, 2002.

Naturally-occurring, spontaneous LDH-deficient *mutans Streptococcus* strains can be prepared using methods disclosed in, for example, Hillman, Lactate dehydrogenase mutants of *Streptococcus mutans*: isolation and preliminary characterization. Infect. Immun. 21:206-212 (1978). Spontaneous LDH-deficient mutants occur at the rate of approximately $10^{-5}$ frequency. See Johnson et al., Cariogenic potential in vitro in man and in vivo in the rat of lactate dehydrogenase mutants of *Streptococcus mutans*. Arch. Oral Biol. 25:707-713 (1980).

Naturally-occurring, spontaneous LDH-deficient strains of *mutans Streptococcus* can be differentiated from LDH-producing strains of *mutans Streptococcus* by plating the bacteria on glucose tetrazolium medium. LDH-deficient *mutans Streptococcus* colonies will be bright red and relatively larger in size than colonies of the parent strain, which are white and relatively smaller in size on the glucose tetrazolium medium. Naturally-occurring, spontaneous LDH-deficient strains of *mutans Streptococcus* can be used in a composition of the invention.

An LDH-deficient strain of *S. rattus* has been isolated. Briefly, a culture of *S. rattus* BHT-2 was grown overnight to saturation in Todd Hewitt broth, and diluted samples were spread on glucose tetrazolium medium to give approximately 300 colonies per plate. Wild-type, acid producing colonies are white on this medium. LDH-deficient mutants are bright red. *S. rattus* JH145 was one red colony amid approximately 100,000 white colonies that were screened. *S. rattus* JH145 is therefore a naturally-occurring, LDH-deficient mutant.

LDH-deficient strains of *mutans Streptococcus*, such as LDH-deficient mutants of *S. rattus* BHT-2, produce less total titratable acid when incubated in the presence of glucose and other sugars or polyols, make substantially less lactic acid when incubated in the presence of glucose in the case of resting and growing cultures, adhere better to hydroxyapatite and accumulate more plaque when grown in the presence of sucrose. LDH activity can be assayed as described by Brown & Wittenberger (J. Bacteriol. 110:604, 1972).

Terminal pH can be determined by subculturing strains (1:100) in Todd-Hewitt broth containing 1% glucose. After 48 hours incubation in candle jars at 370 C, the absorbance at 580 nm and pH of the cultures can be determined. Lactic acid concentration of cultures can be determined by gas-liquid chromatography. See Salanitro & Muirhead, Quantitative method for the gas chromatographic analysis of short-chain monocarboxylic and dicarboxylic acids in fermentation media. Appl. Microbiol. 29:374-381 (1975); Hillman et al., Acetoin production by wild-type strains and a lactate dehydrogenase-deficient mutant of *Streptococcus mutans*. Infect. Immun. 55:1399-1402 (1987). Additionally, any genetic modification techniques known to those of skill in the art can be used to create an LDH-deficient *mutans Streptococcus* strain from an LDH-producing *mutans Streptococcus* parent strain. For example, an LDH gene or a portion of an LDH gene can be deleted or mutagenized, including, for example, insertional mutagenesis techniques. Other mutagenesis techniques include, for example, homologous recombination, recursive sequence recombination, oligonucleotide-directed mutagenesis, site-directed mutagenesis, error-prone PCR, phosphothioate-modified DNA mutagenesis, uracil-containing template mutagenesis, gapped duplex mutagenesis, point mismatch repair mutagenesis, repair-deficient host strain mutagenesis, radiogenic mutagenesis, deletion mutagenesis, restriction-selection mutagenesis, restriction-purification mutagenesis, site saturation mutagenesis, ensemble mutagenesis, recursive ensemble mutagenesis, and chimeric nucleic acid creation. Therefore, any genetic modification technique that disables an LDH gene can be used to produce an LDH-deficient *mutans Streptococcus* strain. In one embodiment of the invention, the LDH-deficient strains, whether naturally-occurring or genetically-modified mutants, have a reversion frequency less than $10^{-7}$ and produce less than about 10% of the parental level of lactate dehydrogenase activity.

The use of two or more different species of bacteria can provide an advantage over using a single species. This is because different species of bacteria colonize different surfaces or portions of teeth. Therefore, the use of more than one species of bacteria can be used to "blanket" all or most surfaces of the teeth, whereas the use of only one species of bacteria may result in certain surfaces or portions of the teeth being uncolonized. Therefore, all surfaces of the teeth are exposed to whitening action.

Compositions of the invention can further comprise one or more carbon sources that are metabolizable by the one or more isolated, non-pathogenic, hydrogen peroxide-producing bacterial species or strains or the one or more lactate dehydrogenase deficient *mutans Streptococcus* species or strains or both types of species or strains. Carbons sources include, but are not limited to, for example, glucose, sorbitol, mannitol, fructose, galactose, maltose, sucrose, xylose, lactose, glycerol or combinations thereof.

The compositions of the invention can comprise a pharmaceutically acceptable or nutritionally acceptable carrier. The carrier is physiologically compatible with the oral cavity of the subject to which it is administered. Carriers can be comprised of solid-based, dry materials for formulation into tablet, capsule, lozenge, or powdered form. A carrier can also be comprised of liquid or gel-based materials for formulations into liquid, gel, and chewing gum forms. Suitable liquid or gel-based carriers include but are not limited to: water, physiological salt solutions, urea, alcohols and derivatives, and glycols (e.g., ethylene glycol or propylene glycol). The composition of the carrier can be varied so long as it does not interfere significantly with the therapeutic activity of the bacterial strains of the invention.

A composition can be formulated to be suitable for oral administration in a variety of ways, for example in a solid, semi-solid, liquid (including, e.g., a viscous liquid, a paste, a gel, or a solution), a dried mass, a dentifrice, a mouth wash, an oral rinse, a liquid suspension, a topical agent, a powdered food supplement, a paste, a gel, a solid food, an oral rinse, a packaged food, a wafer, lozenge, chewing gum and the like. Other formulations will be readily apparent to one skilled in the art. A composition of the invention can include a nutrient supplement component and can include any of a variety of nutritional agents, as are well known, including vitamins, minerals, essential and non-essential amino acids, carbohydrates, lipids, foodstuffs, dietary supplements, and the like.

Compositions of the invention can also include natural or synthetic flavorings and food-quality coloring agents, all of which are compatible with maintaining viability of the bacterial species or strains of the invention.

A composition of the invention can include one or more gelling agents that can act as an adhesive agent to adhere the composition to the teeth. The concentration of the gelling agent may be greater than about 2, 4, 6, 8, 10, 15, 20, 30, 40, 50, 60, 70, 80 or less than about 80, 70, 60, 50, 40, 30, or 20 percent by weight of the composition.

Suitable gelling agents and adhesion agents useful in the present invention include, for example, silicone, polyethylene oxide, polyvinyl alcohol, poly alkyl vinyl ether-maleic acid copolymer (PVM/MA copolymer) such as, Gantrez AN 119, AN 139, and S-97, polyvinyl alcohol, polyacrylic acid, Poloxamer 407 (Pluronic), polyvinyl pyrrolidone-vinyl acetate copolymer (PVP/VA copolymer), such as Luviskol VA, and Plasdone S PVP/VA, polyvinyl pyrrolidone (PVP, e.g., K-15 to K-120), Polyquaterium-11 (Gafquat 755N), Polyquaterium-39 (Merquat plus 3330), carbomer or carboxypolymethylene (Carbopol), hydroxy propyl methyl cellulose, hydroxy ethyl cellulose, hydroxy propyl cellulose, corn starch, carboxymethyl cellulose, gelatin and alginate salt such as sodium alginate, natural gums such as gum karaya, xanthan gum, Guar gum, gum arabic, gum tragacanth, and mixtures thereof.

A humectant or plasticizer can be present in compositions of the invention. Humectants or plasticizers include, for example, glycerin, glycerol, sorbitol, polyethylene glycol, propylene glycol, and other edible polyhydric alcohols. The humectants or plasticizers can be present between at about 1% to about 99%, about 10% to about 95%, or at between about 50% and about 80% (or any range between 1% and 99%) by weight of a composition.

Bacteria of the invention can be prepared in, for example, a fermenter. The bacteria can be harvested from the fermenter and can be, for example, concentrated. Bacteria of the invention can be prepared for use by, for example, dehydration or spray drying. Spray drying generally comprises spraying a suspension of bacteria in a vessel and under a steam of hot air. Bacteria can also be prepared for use by microencapsulation (see e.g., U.S. Pat. No. 6,251,478), freeze-drying, or by coating with a protective substance such as, for example, lipid material such as triacylglycerols, waxes, organic esters, soybean oil, cottonseed oil, palm kernel oil, and esters of long-chain fatty acids and alcohols.

Methods of Whitening Teeth

The invention provides methods for delivering a composition that provides one or more oral care benefits, including tooth whitening, to the surfaces of the oral cavity comprising applying a composition of the invention to the teeth and/or adjacent soft tissue of a subject.

The bacterial species or strains can be present in a composition of the invention in a therapeutically effective amount. Therapeutically effective means effective to alleviate, reduce, prevent and/or ameliorate one or more symptoms of dental caries, periodontitis, bacterial infections or diseases, oral wounds, *Candida* or fungal overgrowth, halitosis, or xerostomia-induced dental caries or periodontal disease or to alleviate, reduce, prevent, or ameliorate stains or discoloration on the teeth either permanently or temporarily. Therapeutically effective also means effective to promote wound healing in an oral cavity.

A therapeutically effective amount is an amount of a composition of the invention at high enough levels to significantly improve the condition to be prevented and/or treated, but low enough to avoid serious side effects (at a reasonable benefit/risk ratio), within the scope of sound medical/dental judgment. The therapeutically effective amount of a composition of the invention may vary with the particular condition being treated, the age and physical condition of the patient being treated, the severity of the condition, the duration of treatment, the nature of concurrent therapy, the specific form of the source employed, and the particular vehicle from which the composition is applied.

The compositions of the invention can be applied in a therapeutically effective amount to the mucosal tissue of the oral cavity, to the gingival tissue of the oral cavity, to the surface of the teeth and/or any combination thereof for the treatment and/or prevention of stained and/or discolored teeth. A composition of the invention may be swallowed or may rinsed around the oral cavity and spit out. Treatment means inducing a reduction in the amount or intensity of discoloration or stains on the teeth. Prevention means that substantially no additional staining or discoloration forms on the teeth, for example, during the treatment period, temporarily (for a period of time after treatment), or permanently. In one embodiment of the invention, a composition is applied solely to the surfaces of the teeth (and optionally to the soft tissues directly surrounding the teeth) to the exclusion of other tissues in the oral cavity. This can be achieved by, for example, directly swabbing a composition of the invention directly onto tooth surfaces or by holding a composition of the invention in place over the teeth with, for example, a barrier layer.

The VITA 3D Master™ Shade Guide provides a range of tooth shades that varies from very light to very dark. A total of 29 tooth shades constitute the entire range of colors between these two endpoints on a scale of brightness. In one embodiment of the invention, methods of the invention provide a change of about 1, 2, 3, 4, 5, 6, 7, 8, 9, 10, 11, 12, 13, 14, 15 or more (or any value or range in between 1 and 29) VITA 3D Master™ shades of brightness.

The bacterial strains of the invention can form at least a part of the transient or indigenous flora of an oral cavity and exhibit additional beneficial prophylactic and/or therapeutic effects in the cavity. Additional oral care benefits of compositions of the invention include, for example, the treatment and/or prevention of dental caries, periodontitis (including, for example, early-onset periodontitis, localized and generalized juvenile periodontitis, and rapidly progressive and adult periodontitis), oral bacterial infections and diseases, oral wounds, *Candida* or fungal overgrowth, halitosis, or xerostomia-induced dental caries, the promotion of wound healing, or a combination thereof in a subject. Treatment means that one or more symptoms of these diseases/conditions are alleviated, reduced, or ameliorated either permanently or temporarily.

In one embodiment of the invention, compositions of the invention can be applied to the teeth of a subject in conjunction with a barrier layer to hold the composition in contact with the teeth and surrounding oral tissues. A barrier layer can be solid or deformable and can hold a composition of the invention in contact with the lingual, facial, occlusal, and/or incisal surfaces of the teeth. A barrier layer can comprise a custom fit or non-custom fit dental treatment tray that includes at least one or two side walls and a bottom wall defining a U-shaped or L-shaped trough. A composition of the invention is present in the trough area of the barrier and the barrier can be placed against the teeth such that the composition of the invention is in contact with the teeth.

Alternatively, the barrier layer can comprise a flexible strip of material. The strip of material can comprise any material, including, for example, one or more polymers, polymeric film, wax, foam, natural and synthetic woven materials, non-woven material, foil, paper, rubber, and combinations thereof. The strip of material can be a single layer of material or a laminate comprising more than one layer. For example, the strip of material can comprise a laminate of two or more polymeric films or can comprise a wax and non-woven material.

The strip of material can have any shape and size that covers the facial, occlusal, incisal, occlusal and/or lingual surfaces of a plurality of teeth and/or some of the soft tissue adjacent the facial, incisal, occlusal, and/or lingual surfaces of a plurality of teeth.

The strip of material can be held in place on the oral surface by adhesive attachment provided by a composition of the invention or any other composition that is applied to, coated on, or intermixed with the strip of material. Alternatively, the strip of material can be held in place by mechanical pressure from deforming the strip of material about the facial, incisal, occlusal, and/or lingual surfaces of the teeth. The strip of material may be dissolvable or erodible. After dissolution or erosion of the strip of material, the composition of the invention can be left behind on the facial, occlusal, incisal, and/or lingual tooth surfaces and/or the soft tissues surfaces to continue to act upon those surfaces.

Compositions can be administered to an oral cavity of a subject such as an animal, including a mammal, for example, a human, a non-human primate, a dog, a cat, a rat, a mouse, a horse, a goat, or a rabbit.

The compositions of the invention can be orally administered in for example, food, water, a dentifrice, a gel, a paste, an emulsion, aerosol spray, chewing gum, lozenge, tablet, capsule, or a liquid suspension. The bacteria can either be already formulated into food, water, gel or other carrier or can be a composition that is added to the carrier by the user prior to consumption.

One embodiment of the invention provides a method of non-persistently colonizing an oral cavity of a subject with therapeutically-effective bacteria comprising administering to the oral cavity of a subject a composition of the invention. In one embodiment of the invention the administered bacterial strains do not permanently colonize the oral cavity, rather the strains are present in the oral cavity for about 1 day, about 1 week, about 2 weeks, about 3 weeks, about 1 month, about 3 months or about 12 months after administration of the bacteria.

Compositions of the invention can be administered at a dose of about $1\times10^3$, $1\times10^5$, $1\times10^7$, $1\times10^9$, or $1\times10^{11}$ CFU (or any range or value between about $1\times10^3$ and about $1\times10^{11}$) of viable bacteria. A dose of a composition of the invention can be administered at three times a day, twice a day, once a day, every other day, two times a week, weekly, biweekly, or monthly. One, two, or more doses of a composition of the invention can be administered per day for about 1 week, about 2 weeks, about 1 month, about 2 months, about 3 months, about a year or more.

Compositions of the invention can be used daily as part of an oral care regimen. Using compositions of the invention as part of a daily oral care regimen allows a user to achieve and sustain a variety of desired oral care benefits, including but not limited to white, tartar-free teeth.

A composition of the invention can be applied to the teeth and/or soft tissue for between about 1 minute and about 8 hours. In some embodiments, the composition can be applied for greater than about 1, 2, 3, 4, 5, 6, 7, 8, 9, 10, 15, 20, 30, 40, 50, 60, 90, 120, 150, 180, 210, 240, 270, 300, 330, 360, 390, 420, 450, 480 minute(s) (or any range or value between about 1 and about 480 minute(s)) and/or less than 480, 450, 420, 390, 360, 330, 300, 270, 240, 210, 180, 150, 120, 90, 60, 50, 40, 30, 20, 15, 10, 9, 8, 7, 6, 5, 4, 3, 2 or 1 minute(s) (or any range or value between about 480 and about 1 minute(s)) and any combination thereof, wherein the bacterial species or strains have a concentration between about 0.01% and about 50%, or about 0.1% to about 25%, or about 1.0% to about 10% or any ranges or values in between 0.01% and 50% by weight of the composition. Such a regimen could be advantageously used once a day for greater than about one month, two months, four months, six months, twelve months, eighteen months, two years, five years, eight years, ten years and/or less than about fifteen years, ten years, eight years, five years, two years, 18 months, 12 months, six months, four months, two months, one month and any combination thereof. In another embodiment such a regimen could be advantageously used once or twice a day for greater than about one month and less than about 5 years.

A kit of the invention can contain a one month, two month, three month, four month, five month, six month, or 12 month supply of a composition of the invention. A composition of the invention can be packaged and, in turn, a plurality of the packaged compositions can be provided in a storage container or outer package or carton.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

The natural *viridans* streptococci strains *Streptococcus oralis* (KJ3sm) and *Streptococcus uberis* (KJ2sm) can promote periodontal health by production of hydrogen peroxide, which inhibits the growth of periodontal pathogens. Hydrogen peroxide production is a normal end product of glycolysis when these microorganisms are incubated in the presence of a sugar, such as glucose or sucrose, and there is oxygen present in the atmosphere.

Stained dental ceramic material, representative of stained dental enamel, was treated with a suspension of *S. oralis* to determine if *S. oralis* can promote tooth whitening. Therefore, a suspension of *S. oralis* was incubated in vitro in the presence of glucose and oxygen, to determine if it could produce sufficient hydrogen peroxide to enable a measurable whitening effect on stained ceramic disks resembling teeth.

Ten dental ceramic disks (courtesy of Dr. Kenneth J. Anusavice, University of Florida, Gainesville, Fla.) were stained over an eight-week period with tea (Lipton) and chlorhexidine (0.12%, Hi Tech Phamacal Co., Amityville, N.Y.). Each disk was placed in a 50 ml conical (Falcon) plastic test tube. Three ml of brewed Lipton tea (prepared by the addition of a family size Lipton tea bag to 200 ml of boiling water for 5 min) was added to cover the disks. After 24 hr incubation at room temperature, the tea was removed by decanting, the disk was rinsed with 5 ml of tap water, and the tea solution was replaced with 3 ml of 0.12% chlorhexidine for 24 hrs. Steps 2 and 3 were repeated for 4 weeks, Monday through Friday, and the disks remained in Friday's solution over the weekend. The lightness of the disks was quantitatively measured using A Chroma Meter CR-400 calorimeter (Minolta, Ramsey, N.J.). Lightness values for the disks were generated directly by placing the instrument's measuring head over the disks. Standard color plates were used to calibrate the calorimeter.

The treatment phase began one day after the final calorimeter readings were taken. Nine separate cultures of *S. oralis*, strain KJ3sm, inoculated from starter plates, were grown in 30 ml of Todd Hewitt Broth (Difco; Bacto Catalog No. 249240) supplemented with 0.1% sodium bicarbonate/0.5% glucose/1 mg/ml streptomycin sulfate in an environmental shaker (200 rpm) at 37° C. After overnight incubation, the cells were harvested by centrifugation at room temperature, washed once with 10 ml of Amies media, and resuspended in 30 ml of Amies media with or without dextrose (glucose; Fisher Scientific, Catalog No. D16) and catalase (Sigma Aldrich Catalog No. C93225G) as shown in Table 1. The control (Group D) contained 30 ml of Amies medium with dextrose and inactivated catalase. Where indicated, catalase was inactivated by heating in a boiling water bath for 5 minutes. The entire 30 ml aliquots described in step 2 and FIG. 1 were added to 50 ml Falcon tubes containing 1 stained dental ceramic disk per tube. These treatment steps were repeated daily, Monday through Friday, for 4 weeks, and the disks remained in Friday's solution over the weekend.

TABLE 1

| | | TREATMENT CONDITIONS | | |
|---|---|---|---|---|
| GROUP | DISK NUMBER | KJ3sm (~$10^9$ cfu/ml) | Dextrose (0.5%) | Catalase (3000 U/ml) |
| A[1] | 1, 2, 3 | + | + | Inactivated |
| B[2] | 4, 5, 6 | + | + | Active |
| C[3] | 7, 8, 9 | + | − | Inactivated |
| D[4] | 10 | − | + | Inactivated |

[1]Experimental
[2]Catalase control
[3]Dextrose control
[4]Amies control

Figure 2:
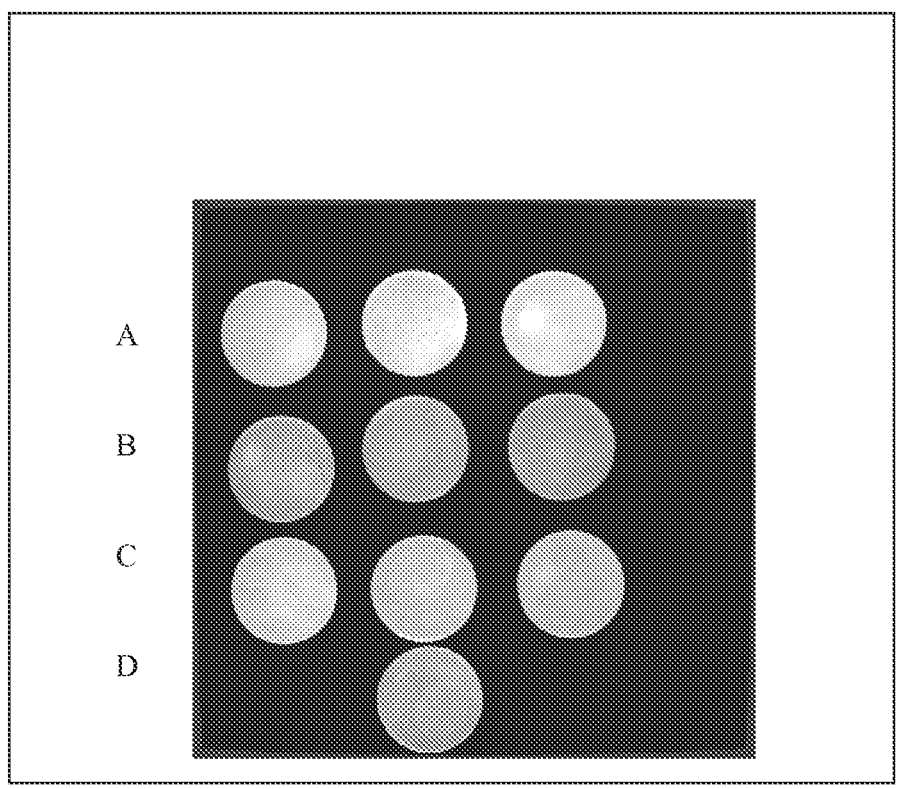
FIG. 2 shows the visual appearance of stained ceramic disks following treatment for 4 weeks. Group A (Experimental), Group B (plus catalase), Group C (minus dextrose), D (minus KJ3 sm).

The lightness value for each disk was measured weekly during the treatment phase, which was carried out over a four-week period. The L value (lightness) was plotted as a function of time using the mean group values (±S.D.; FIG. 1). The trendline for Group A data had a slope of 2.37, which was substantially greater than the slopes of the trendlines for Group B (−0.54), Group C (0.52) and Group D (−0.84), indicating that disks in Group A were becoming lighter or whiter over time at a much faster rate than the disks in the other groups. At the conclusion of the 4 week experimental period, a lightening or whitening of the ceramic disks in group A was readily apparent to the unaided eye (FIG. 2).

Inter- and intra-group L values were compared for statistically significant differences. A 4 (Treatments: A, B, C, D)×5 (Time: Weeks 0, 1, 2, 3, 4) mixed-model repeated measures ANOVA was conducted with Greenhouse-Geisser correction to determine the differential influence of various treatments on L values across time. Follow-up analyses determined treatment effects at each time point. Post hoc Bonferroni-corrected t tests were used to determine significant differences among the treatments. All analyses used a family-wise of p=0.05. Results indicated significant effects of Treatment, $F (3, 6)=6.0$, $p<0.05$, and Time, $F (1.3, 24)=12.7$, $p=0.005$, which were superseded by a Treatment× Time interaction, $F (4, 24)=58.7$, $p<0.001$. Decomposition of this interaction yielded non-significant findings at baseline (Time 0) and Week 1, $F (3, 6)<4.4$, $p>0.05$. At Weeks 2-4, Treatment Group A yielded a significantly larger effect than Treatments B and D, $t (3)>8.1$, $p<0.01$, and a significantly larger effect than Treatment C only during week 4, $t (2)=4.1$, $p=0.015$. No significant differences were observed between Treatments B, C, and D ($p>0.05$).

*S. oralis* incubated in the presence of glucose and air produced a statistically significant whitening effect on tea and chlorhexidine-stained ceramic disks after 4 weeks of exposure to *S. oralis*. Inclusion of catalase in the incubation medium significantly reduced any whitening effect, suggesting that the mechanism of whitening involved hydrogen peroxide production by the cells. Peroxide production, and thus a whitening effect, was dependent on the presence of a metabolizable carbon source, such as glucose. The small whitening effect observed in Group C may be due to residual peroxide production resulting from metabolism of stored carbohydrate (e.g., in the form of intracellular polysaccharide). The plot of L value as a function of time for Group A in FIG. 1 did not plateau, indicating that maximum whitening effect had not occurred within the timeframe of the study, and that longer treatment with KJ3sm would likely achieve a greater whitening effect.

What is claimed is:

1. A dental treatment device comprising:
   a bacteria formulation comprising (1) an isolated, non-pathogenic, hydrogen peroxide producing bacterial species or strain selected from a hydrogen peroxide-producing *viridans* Streptococci species or strain; a hydrogen peroxide producing *Lactobacillus* species or strain, a hydrogen peroxide producing *Lactococcus* species or strain; a hydrogen peroxide producing *Pediococcus* species or strain, and a hydrogen peroxide producing *Leuconostoc* species or strain in an amount sufficient to provide at least 0.5 mM hydrogen peroxide, (2) a lactate dehydrogenase (LDH)-deficient *Streptococcus*, and (3) a carbon source metabolizable by both (1) and (2); and
   a dental treatment tray comprising at least one sidewall and a bottom wall that define a trough,
   wherein the bacterial formulation is present in the trough.

2. The bacterial composition of claim 1, wherein the LDH-deficient *Streptococcus* comprises a genetically modified strain of *Streptococcus mutans*.

3. The dental treatment device of claim 1, wherein the dental treatment tray is custom fitted to an individual in need of treatment.

4. The dental treatment device of claim 1, wherein the dental treatment tray is not custom fitted.

5. The dental treatment device of claim 1, wherein the dental treatment tray comprises one sidewall and wherein the trough has an L shape.

6. The dental treatment device of claim 1, wherein the dental treatment tray comprises two side walls and has a U shape.

7. The dental treatment device of claim 1, wherein the dental treatment tray is configured to be placed against teeth of an individual on application of the dental treatment device, such that the bacterial composition is held in contact with said teeth.

8. A method of whitening teeth, comprising inserting a dental treatment device of claim 1 into an oral cavity of an individual in need of treatment.

9. A method of treating oral disease, comprising inserting a dental treatment device of claim 1 into an oral cavity of an individual in need of treatment.

10. The dental treatment device of claim 1, wherein the bacterial formulation further comprises a humectant, and wherein the humectant comprises 50% to 80% of the bacterial formulation.

11. The dental treatment device of claim 1, wherein the isolated, non-pathogenic, hydrogen peroxide producing bacterial species or strain is selected from the group consisting of *Streptococcus oralis* and *Streptococcus uberis*, and wherein the lactate dehydrogenase (LDH)-deficient *Streptococcus* is selected from the group consisting of *Streptococcus rattus* JH145 and *Streptococcus rattus* JH140.

* * * * *